(12) United States Patent
Agrawal et al.

(10) Patent No.: US 11,854,694 B2
(45) Date of Patent: Dec. 26, 2023

(54) RELEVANCE FEEDBACK TO IMPROVE THE PERFORMANCE OF CLUSTERING MODEL THAT CLUSTERS PATIENTS WITH SIMILAR PROFILES TOGETHER

(71) Applicant: KONINKLIJKE PHILIPS N.V., Eindhoven (NL)

(72) Inventors: Vartika Agrawal, Cambridge, MA (US); Alexander Ryan Mankovich, Boston, MA (US); Nevenka Dimitrova, Pelham Manor, NY (US); Nilanjana Banerjee, Armonk, NY (US); Yee Him Cheung, Boston, MA (US); Johanna Maria De Bont, Eindhoven (NL); Jozef Hieronymus Maria Raijmakers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 770 days.

(21) Appl. No.: 16/084,800

(22) PCT Filed: Mar. 8, 2017

(86) PCT No.: PCT/IB2017/051345
§ 371 (c)(1),
(2) Date: Sep. 13, 2018

(87) PCT Pub. No.: WO2017/158472
PCT Pub. Date: Sep. 21, 2017

(65) Prior Publication Data
US 2019/0079938 A1    Mar. 14, 2019

Related U.S. Application Data

(60) Provisional application No. 62/309,067, filed on Mar. 16, 2016.

(51) Int. Cl.
*G06F 16/35* (2019.01)
*G16H 40/63* (2018.01)
(Continued)

(52) U.S. Cl.
CPC ........... *G16H 40/63* (2018.01); *G06F 16/355* (2019.01); *G06F 16/358* (2019.01);
(Continued)

(58) Field of Classification Search
CPC ................. G06F 16/355; G06F 16/358; G06F 19/30–36; G16H 10/60; G16H 50/70; G16H 40/63; G06K 9/6247
See application file for complete search history.

(56) References Cited

U.S. PATENT DOCUMENTS 6,611,846 B1   8/2003  Stoodley
7,809,660 B2   10/2010  Friedlander et al.
(Continued)

FOREIGN PATENT DOCUMENTS

WO    2012149380 A1    11/2012
WO    2015006643 A2    1/2015

*Primary Examiner* — Robert W Beausoliel, Jr.
*Assistant Examiner* — Nirav K Khakhar (57) ABSTRACT

In patient cohort identification, clustering (30) of patients is performed using a patient comparison metric dependent on a set of features (24). Information is displayed on sample patients who are similar or dissimilar to a query patient according to the clustering. User inputted comparison values are received comparing the sample patients with the query patient. The set of features and/or feature weights are adjusted to generate an adjusted patient comparison metric having improved agreement with the user inputted comparison values. The clustering is repeated using the adjusted patient comparison metric. A patient cohort is identified from a cluster (34) containing the query patient produced by the last clustering repetition. The information on the sample patients may be shown by simultaneously displaying two or (Continued)

more graphical modality representations (70, 72, 74) each plotting the sample patients and the query patient against two or more features of the modality.

13 Claims, 5 Drawing Sheets

(51) Int. Cl.
  *G16H 50/70* (2018.01)
  *G06F 18/2135* (2023.01)
  *G16H 10/60* (2018.01)

(52) U.S. Cl.
  CPC ......... *G06F 18/2135* (2023.01); *G16H 10/60* (2018.01); *G16H 50/70* (2018.01)

(56) References Cited

U.S. PATENT DOCUMENTS

| | | |
|---|---|---|
| 8,589,187 B2 | 11/2013 | Gillam et al. |
| 2003/0018629 A1* | 1/2003 | Namba ................ G06F 16/355 |
| 2005/0210015 A1 | 9/2005 | Zhou et al. |
| 2011/0022622 A1 | 1/2011 | Boroczky |
| 2012/0041779 A1 | 2/2012 | Boroczky et al. |
| 2012/0078522 A1 | 3/2012 | Avinash et al. |
| 2012/0317127 A1 | 12/2012 | Friedlander et al. |
| 2013/0231953 A1 | 9/2013 | Ebadollahi et al. |
| 2014/0108379 A1 | 4/2014 | Gotz et al. |
| 2015/0095056 A1 | 4/2015 | Ryan et al. |
| 2015/0161332 A1 | 6/2015 | Simms, Jr. et al. |

* cited by examiner

It appears that patients Pam Brown and Mindy Red are two sample patients who are similar to Jane Smith.

To provide improved identification of a cohort of patients who are similar to Jane Smith, please answer the questions below.

1. Please rank similarity of Pam Brown to Jane Smith on a scale of 1-5 where "1" is most similar and "5" is least similar (i.e. most dissimilar).

Select one: ① ② ③ ④ ⑤

2. Please indicate which of the two patients Pam Brown or Mindy Red you consider to be to be most similar to Jane Smith.

Select one: (Pam Brown) (Mindy Red)

Note: You may click on any patient name above to review the patient's medical record in a pop-up window.

RELEVANCE FEEDBACK TO IMPROVE THE PERFORMANCE OF CLUSTERING MODEL THAT CLUSTERS PATIENTS WITH SIMILAR PROFILES TOGETHER

CROSS-REFERENCE TO PRIOR APPLICATIONS

This application is the U.S. National Phase application under 35 U.S.C. § 371 of International Application No. PCT/IB2017/051345, filed on Mar. 8, 2017, which claims the benefit of U.S. Provisional Application Ser. No. 62/309,067, filed Mar. 16, 2016. These applications are hereby incorporated by reference herein, for all purposes.

FIELD

The following relates generally to the medical arts, electronic clinical decision support (CDS) arts, clinical study arts, genomics arts, and related arts.

BACKGROUND

Numerous medical tasks benefit from identifying cohorts of patients having relevant similarities. For example, a key initial step in designing a clinical trial is to identify patients for enrollment in the clinical trial. To ensure validity of the results, the enrolled patients should be sufficiently similar to one another so that different patient outcomes can be reliably ascribed to the target of the clinical trial (e.g. a new pharmaceutical drug) rather than to differences in patient outcomes due to extraneous factors such as differences in age, gender, ethnicity, presence/absence of chronic medical conditions or so forth (where these are unrelated to the target of the clinical trial). The task of identifying suitable patients to enroll in the clinical trial is difficult, as patient outcome can be affected by many related factors.

Cohort identification can also come into effect after enrollment, during the analysis of results of the clinical trial. Within the enrollment, the patients with positive versus negative outcomes naturally form two cohorts of interest. However, these cohorts may be further segmented based on similarities and distinctions within the positive and negative cohorts, to identify and account for any extraneous factors that may be affecting the raw data results of the clinical trial.

Similar cohort identification tasks are performed in other types of medical studies, for example to assess disease risk factors or in performing "meta-studies" combining data from numerous previous studies.

Other medical tasks include clinical diagnosis and treatment of a patient. In such tasks, the clinician can benefit from comparing the current patient with similar past patients. Again, the task of identifying "similar" patients is challenging. No two patients are the same, and the cohort selection task requires assessing which differences are significant versus insignificant.

The following discloses a new and improved systems and methods that address the above referenced issues, and others.

SUMMARY

In one disclosed aspect, a patient cohort identification device is disclosed. A computer has a display component and at least one user input device. The computer is in communication with a patient database storing patient data comprising values of features for patients in the patient database. The computer is programmed to perform a patient cohort identification method including the following. An automatic feature selection process is performed on the patient data to select a set of features, and automated clustering of patients of the patient database is performed using a patient comparison metric dependent on the set of features. At least one iteration is performed which includes: displaying, on the display component, information on one or more sample patients who are similar or dissimilar to a query patient according to the automated clustering; receiving, via the at least one user input device, user inputted comparison values comparing the one or more sample patients with the query patient; adjusting the patient comparison metric to increase agreement between the user inputted comparison values and comparison values computed by the patient comparison metric comparing the one or more sample patients with the query patient, wherein the adjusting including adjusting at least one of the set of features and feature weights of the patient comparison metric; and repeating the automated clustering using the adjusted patient comparison metric. A patient cohort for the query patient is identified using the adjusted patient comparison metric produced by the last iteration.

In another disclosed aspect, a patient cohort identification device is disclosed. A computer has a display component and at least one user input device. The computer is in communication with a patient database storing patient data comprising values of features for patients in the patient database. The computer is programmed to perform a patient cohort identification method including: simultaneously displaying, on the display component, two or more graphical modality representations in which each graphical modality representation plots patients of the database against two or more coordinate features of the modality; receiving a selection of a cluster of patients in one graphical modality representation; and, in response to receiving the selection, highlighting the patients of the selected cluster of patients in the other simultaneously displayed graphical modality representation or representations.

In another disclosed aspect, a patient cohort identification method is disclosed, which is performed in conjunction with a computer having a display component and at least one user input device and which is in communication with a patient database storing patient data comprising values of features for patients in the patient database. The patient cohort identification method includes the following. Automated clustering of patients of the patient database is performed using a patient comparison metric dependent on a set of features. At least one iteration is performed including: displaying, on the display component, information on one or more sample patients who are similar or dissimilar to a query patient according to the automated clustering; receiving, via the at least one user input device, user inputted comparison values comparing the one or more sample patients with the query patient; adjusting at least one of the set of features and feature weights of the patient comparison metric to generate an adjusted patient comparison metric having improved agreement with the user inputted comparison values as compared with the patient comparison metric without the adjusting; and repeating the automated clustering using the adjusted patient comparison metric. A patient cohort for the query patient is identified as at least part of a cluster containing the query patient produced by the automated clustering repetition of the last iteration.

One advantage resides in providing relevance feedback from the clinician for improved cohort selection.

Another advantage resides in providing relevance feedback for cohort selection based on holistic patient-level analyses by the clinician.

Another advantage resides in providing relevance feedback from a clinician for selection of relevant features without the clinician performing feature-level analysis.

Another advantage resides in providing a graphical user interface via which a clinician can visualize interrelationships of different modalities (clinical, radiology, genomics, demographic, physiological, and so forth).

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

It is recognized herein that the complexity in selecting cohorts can be reduced by selecting an appropriate (reduced) patient features set for grouping patients into cohorts. The patient features set used to select the cohort should include those patient features are relevant for the medical task at hand (e.g. choosing patients to enroll in a clinical trial, or choosing patients similar to the patient currently under clinical diagnosis, et cetera), and should not include those patient features that are not relevant to that medical task. Feature selection is nontrivial because the number of available patient features is typically quite large, and may for example include: demographic data (age, gender, weight, ethnicity, et cetera); presence/absence of chronic behavioral conditions (smoking, heavy alcohol consumption, consumption of various recreational drugs, et cetera); presence/absence of various chronic clinical conditions (high blood pressure, diabetes, asthma, heart disease; et cetera); presence/absence of various acute ailments (pneumonia or other acute respiratory ailments, various oncological conditions, or so forth); features related to same (e.g., cancer stage and grade); and so forth. The rapidly developing field of genomics is quickly adding to the list of available patient features, as genetic sequencing can provide a wealth of genomic markers with varying known or suspected correlations with various medical conditions. For example, some medical databases contain data defining a few hundred or more features, while continued expansion of availability of genomic data could increase the number of features for a patient into the thousands. Such large feature spaces present a significant challenge for selecting a "best" feature set for choosing cohorts for a clinical task.

Numerous unsupervised (reduced) feature set selection techniques are known. A typical automated feature selection technique measures the discriminative power of features, and selects the most discriminative features. One such technique is Principal Component Analysis (PCA), which selects features so as to capture the variance of a data set with a reduced number of features. Other discrimination metrics can be employed, such as information gain (IG) per feature or various pairwise feature correlation metrics (e.g., selecting features providing the highest IG, or eliminating features that are strongly correlated with other features).

Although powerful, unsupervised automatic feature set selection techniques have significant limitations when used to select features for identifying patient cohorts. Highly discriminative features that do not correlate with the clinical task can be selected over other features with lower discriminative power but that do correlate with the medical task. Unsupervised feature set selection techniques are also unable to take into account physiological rationales as to why a particular feature should be probative. For example, consider a suspected clinical condition that is due to a problem with a certain metabolic pathway. A genomic marker that is known to be part of that metabolic pathway is likely to be relevant in this case, but PCA or another unsupervised feature selection technique may fail to select this genomic marker if its overall discriminative power is low.

In principle, these problems could be alleviated by manual feature selection performed by a clinician, or a hybrid approach in which a physician reviews and adjusts an initial feature set generated by unsupervised automatic feature selection (relevance feedback). However, in practice the clinician may not be able to articulate, in terms of specific features, why a patient is considered similar or dissimilar to patient of interest (referred to herein as the "query patient"). A clinician tends to view a patient holistically, in terms of the totality of the physician's past experience and training. Thus, the clinician may recognize a certain patient is similar to, or not similar to, the query patient without being able to precisely articulate which features effectively encapsulate the similarity or dissimilarity. Moreover, it may not be practical to have a skilled clinician take the time necessary to sift through hundreds of available candidate features to identify the probative features for a given clinical task.

Techniques disclosed herein overcome these difficulties by combining unsupervised feature selection with subsequent relevance feedback provided by a clinician at the patient level through review of automated clustering performed using the automatically selected features set. In these approaches, the initial automated features set is used to perform unsupervised automated patient clustering to identify a cluster of patients including the query patient and other clusters. The cluster containing the query patient defines a set of similar patients according to the initial feature set, while other clusters group various less similar patients. The clinician then reviews these clustering results and selects similar or dissimilar patients (the relevance feedback). The feature set is then adjusted automatically to better conform to these clinician selections, and the clustering is repeated with the adjusted feature set. This process can be repeated until the unsupervised automated clustering produces clusters that are (at least substantially) satisfactory to the clinician.

This approach leverages the power of unsupervised feature set selection to provide an initial approximate culling of the large features space. Using the initial feature set generated by PCA or another unsupervised feature selection process, patients are clustered to identify similar (or dissimilar) patients respective to a query patient as measured using this initial feature set. The clinician is presented with one or more similar (or dissimilar) sample patients, and is provided with a user interface via which the clinician may provide relevance feedback. For example, the physician may be presented with a set of similar sample patients {$P_C$} which are identified in the initial clustering as being similar to a patient being diagnosed (the query patient $P_Q$). These "similar" sample patients may, for example, be drawn from the same cluster to which the clustering assigns the query patient $P_Q$, or a sub-set of that cluster having the shortest distance $|P_Q-P_C|$ using a distance metric defined by the initial feature set. The physician can then rank the patients as similar or dissimilar to the query patient $P_Q$ using a ranking scale 1 . . . 5 where 1 indicates most similar and 5 indicates most dissimilar. Thereafter, a feature set adjustment is performed to generate an adjusted feature set that more closely aligns with the physician's similarity rankings for the considered patients. The clustering is again repeated and the cluster containing query patient $P_Q$ or some sub-set thereof is again presented to the physician for similarity ranking. This process may be repeated until the physician is satisfied that the cluster containing query patient $P_Q$ is a suitable cohort for performing the medical task at hand.

Advantageously, this approach for relevance feedback does not require the clinician to evaluate the feature set at the abstracted level of the feature space. Rather, the clinician operates in the more familiar setting of comparing and contrasting individual patients, so that the clinician can leverage the totality of the physician's past experience and training in making relevance feedback decisions. Preferably, the user interface enables the physician to look up the complete medical record of each proposed similar patient $P_C$ under consideration, as well as the complete medical record of the query patient $P_Q$, in order to make the relevance feedback evaluation using the same sources of information the clinician is used to accessing.

Figure 1:
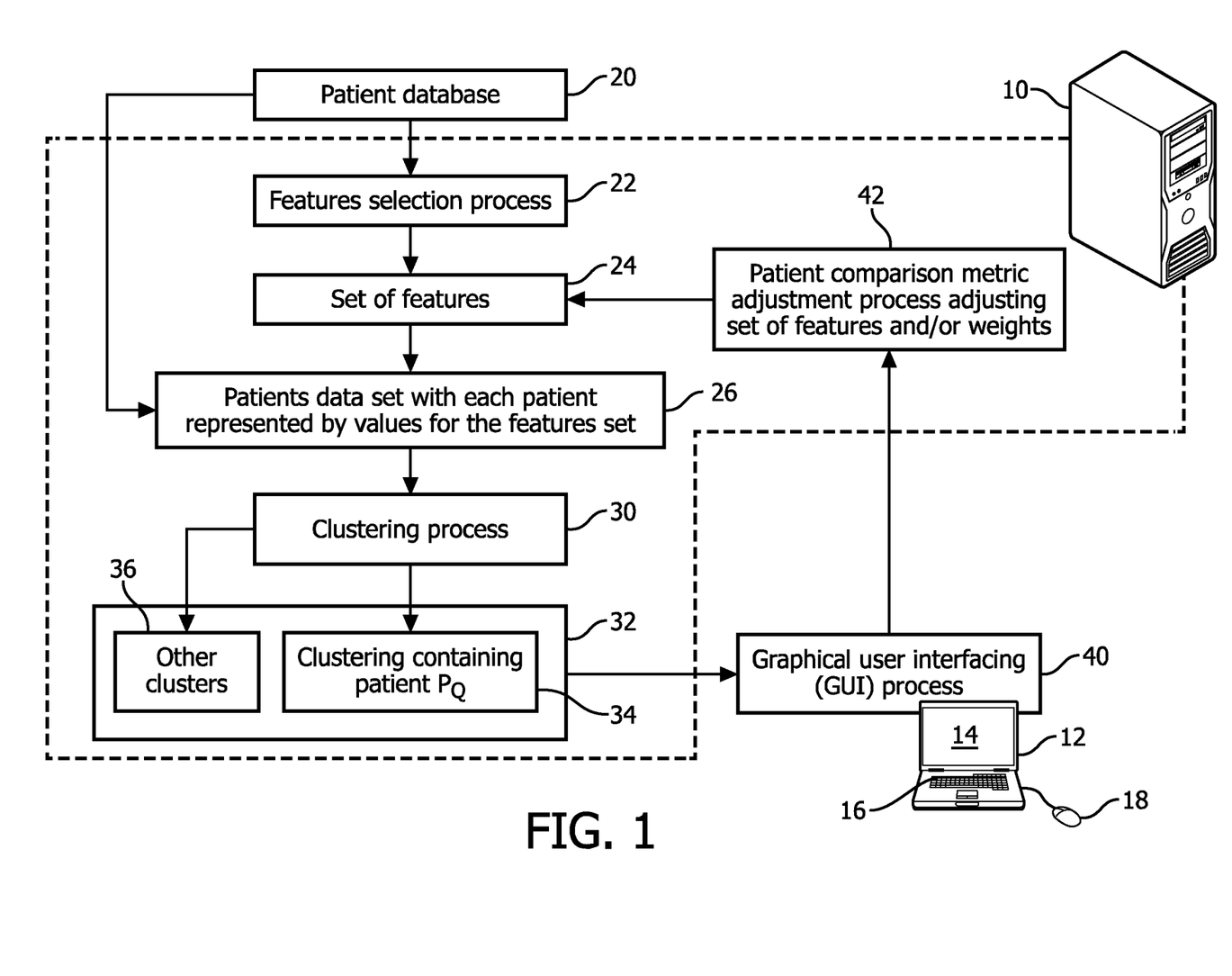
FIG. 1 diagrammatically illustrates a patient cohort identification device.

With reference to FIG. 1, a patient cohort identification device includes a computer having a display component and at least one user input device. The illustrative computer includes two computers: a server computer 10 that performs computationally intensive operations such as feature selection or clustering, and a user interfacing computer 12 such as a desktop computer, notebook computer, tablet computer, or so forth, that includes or is operatively connected with a display component 14 and at least one user input such as an illustrative keyboard 16 and a mouse 18 (or trackball, trackpad, touchscreen, or other pointing device). The computer 10, 12 is in communication with a patient database 20 that stores patient data comprising values of features for patients in the patient database. The patient database 20 may, for example, include one or more of an Electronic Health Record (EHR), Electronic Medical Record (EMR), a Picture Archiving and Communication System (PACS, used for radiology images/data), a Cardiovascular Information System (CVIS), various combinations thereof, or so forth. The various components 10, 12, 20 may be interconnected by various data paths such as a hospital Local Area Network (LAN), Wireless LAN (WLAN), the Internet, various combinations thereof, or so forth.

The computer 10, 12 is programmed to implement various processes. An automatic feature selection process 22 is performed to select a reduced set of features from the typically much larger set of available features contained in the patient database 20 or derivable from information contained in the patient database 20. The feature selection process 22 may, for example, be a Principal Component Analysis (PCA) feature selection process, an Information Gain (IG) feature ranking process, a pairwise correlated feature removal process, or so forth. The automatic feature selection process 22 identifies a set of features 24, typically choosing features with high discriminative power. It will be appreciated that the patient database 20 may store (explicitly or implicitly, i.e. derivable from other stored information) dozens, hundreds, or more features for each patient. Some non-limiting illustrative features include: demographic features (patient age, gender, weight, ethnicity, et cetera); features indicating the presence or absence of chronic behavioral conditions (smoking, heavy alcohol consumption, consumption of various recreational drugs, et cetera); features indicating the presence or absence of various chronic clinical conditions (high blood pressure, diabetes, asthma, heart disease; et cetera); features indicating the presence or absence of various acute ailments (pneumonia or other acute respiratory ailments, various oncological conditions, or so forth); condition-specific features such as cancer stage, cancer grade; genomic features such as values of specific genes, various protein expression levels or other genetic markers; and so forth. A patient data set 26 is thus generated, in which each patient is annotated or represented by values drawn from the patient database 20 for the features of the set of features 24.

A clustering process 30 performs unsupervised learning to group patients of the patient data set 26 into a set of clusters 32. In general, the goal is to identify a patient cohort of patients who are similar to a query patient $P_Q$ thus, the set of clusters 32 include: a cluster 34 containing query patient $P_Q$ (or, said another way, the cluster 34 is the cluster produced by the clustering process 30 to which the query patient $P_Q$ belongs); and other clusters 36 generated by the clustering process. The clustering process may employ any known clustering approach, such as k-means clustering, connectivity-based or hierarchical clustering, centroid-based clustering, expectation-maximization (EM) clustering, or so forth. The clustering uses a patient comparison metric that is dependent on the set of features 24. For two patients $P_i$ and $P_j$ the value of the patient comparison metric comparing these two patients is written herein using the shorthand notation $|P_i-P_j|$. By way of non-limiting illustration, the patient comparison metric may be a distance metric whose value is smaller for more similar patients. Some suitable distance metrics are the Euclidean distance:

$$d_{Euclidean}(P_i, P_j) = \sqrt{\sum_{n=1}^{N} w_n (f_{n,i} - f_{n,j})^2} \tag{1}$$

where n=1, N indexes the features of the set of features 24, $f_{n,i}$ and $f_{n,j}$, are the values of the nth feature for patients $P_i$ and $P_j$, respectively, and $w_n$ is the feature weight for the nth feature in the Euclidean distance of Expression (1). As another example, the patient comparison metric can be the Euclidean squared distance which is identical with Expression (1) except that the square-root is omitted. Instead of a distance metric, the patient comparison metric could alternatively be a similarity metric whose value is larger for more similar patients. These are merely illustrative examples. In general, the patient comparison metric is preferably functionally dependent on the set of features 24 with the contributions of individual features being controlled by feature weights (e.g. feature weights $w_n$ in the illustrative Euclidean distance of Expression (1)). It is also contemplated to employ a patient comparison metric that does not include adjustable feature weights.

For a chosen clustering process 30, the characteristics of the clustering result 32 depend on the particulars of the patient comparison metric, especially the set of features 24 upon which the patient comparison metric is functionally dependent, and the feature weights (if adjustable). The automated feature selection process 22 selects features based on assessment of their discriminative capabilities, but this approach can choose highly discriminative features over features with lower discriminative power that more strongly correlate with the medical task at hand, or features that have some physiological basis for being relevant to the task at hand.

In the illustrative patient cohort identification device of FIG. 1, these concerns are addressed by providing relevance feedback to improve the patient comparison metric, e.g. by adjusting the set of features 24 and/or the feature weights. To this end, a graphical user interfacing (GUI) process 40 is implemented, e.g. on the computer 12 in the illustrative embodiment. The GUI process 40 presents (on the display component 14) information on one or more sample patients who are similar or dissimilar to a query patient $P_Q$ according to the automated clustering. For example, the sample patients may be similar sample patients (pseudo)randomly selected from the cluster 34 containing the query patient $P_Q$. Alternatively, the similar sample patients may be selected from this cluster 34 non-randomly, e.g. selecting patients closest to the query patient $P_Q$ as measured by the patient comparison metric. Additionally or alternatively, dissimilar sample patients may be selected from the other clusters 36, e.g. randomly or from other clusters whose centroids are furthest from query patient $P_Q$ as measured by the patient comparison metric. The sample patients are presented to the user via the display component 14 with the clinician requested to provide comparison values comparing the one or more sample patients with the query patient. For example, the clinician may be requested to rank similarity of a sample patient to the query patient on a scale of 1-5 (or on a scale of 1-10, or so forth). Additionally or alternatively, the clinician may be requested to select which of two sample patients is most similar to the query patient. It will be noted that such approaches do not (at least directly) ask the clinician to evaluate similarities at the feature level, but rather ask for evaluation at the patient level. This leverages the strength of a typical clinician who is typically trained to analyze a patient on the basis of all available information in the patient record together with the clinician's education and experience. This approach avoids asking the physician to perform feature-level analysis which is not the natural operational sphere of a clinician.

The GUI process 40 receives, via the at least one user input device 16, 18, user-inputted comparison values comparing the one or more sample patients with the query patient. This constitutes the "relevance feedback". A patient comparison metric adjustment process 42 then adjusts the set of features 24, and/or adjusts the feature weights $w_n$, to increase agreement between the user-inputted comparison values and comparison values computed by the patient comparison metric comparing the one or more sample patients with the query patient $P_Q$.

In one approach, the patient comparison metric adjustment process 42 performs feature set adjustment iterations, each of which is performed as follows. In the first step of an iteration, the set of features 24 is adjusted by adding a feature to the set, or by removing a feature from the set, to produce a candidate adjusted set of features. Comparison values are then computed, using the patient comparison metric with the candidate adjusted set of features, that compare the one or more sample patients with the query patient $P_Q$. The candidate adjusted set of features is accepted or rejected based on whether the comparison values computed are in increased or decreased agreement, respectively, with the user-inputted comparison values. If rejected, then the candidate adjusted set of features is discarded. If accepted, then the candidate adjusted set of features becomes the new (i.e. updated) set of features 24. This process can be repeated a fixed number of times, or can be repeated until several successive iterations result in rejection, or some other stopping criterion can be used.

In another approach, the patient comparison metric adjustment process 42 performs feature weights adjustment iterations, each of which is performed as follows. In a first step of an iteration, the patient comparison metric is adjusted by increasing or decreasing the value of at least one feature weight of the patient comparison metric to produce a candidate adjusted patient comparison metric. Comparison values are computed using the candidate adjusted patient comparison metric that compare the one or more sample patients with the query patient. The candidate adjusted patient comparison metric is accepted or rejected based on whether the comparison values are in increased or decreased agreement, respectively, with the user-inputted comparison values. If accepted then the new feature weight(s) are used; if rejected then they are discarded.

Figure 2:
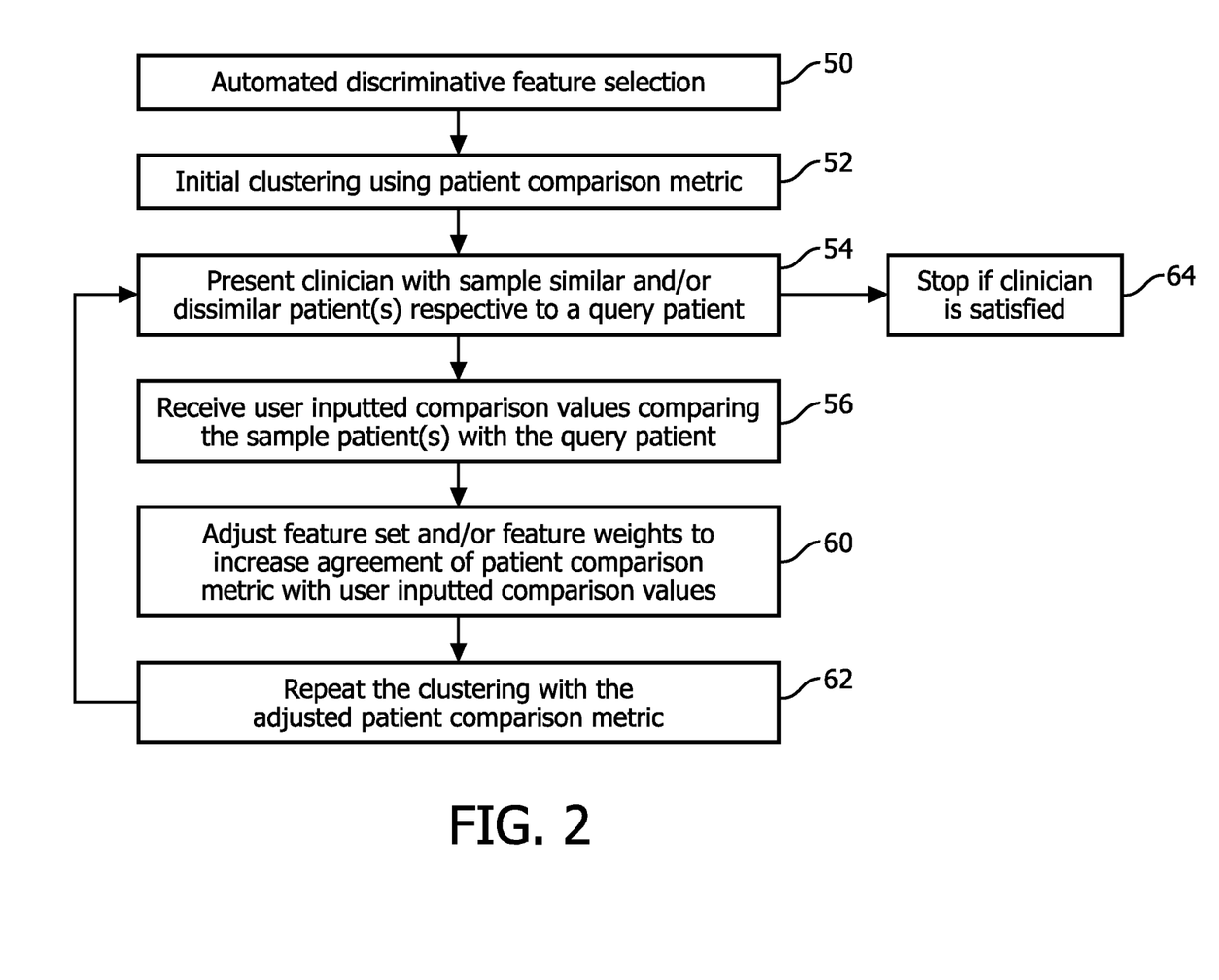
FIG. 2 diagrammatically illustrates a patient cohort identification method suitably performed by the patient cohort identification device of FIG. 1.

With reference now to FIG. 2, a process performed using the patient cohort identification device of FIG. 1 is described. In an operation 50, the feature selection process 22 is performed to select the (initial) set of features 24. In an operation 52, the clustering process 30 is performed to generate (initial) clusters 32. In an operation 54, the clinician is presented with one or more similar and/or dissimilar sample patients, where similarity/dissimilarity is measured with respect to the query patient $P_Q$ using the patient comparison metric. More particularly, information on the sample patients is presented, preferably in the form of a request for information formulated in a manner familiar to the clinician, such as ranking similarity of the sample patient to the query patient, or a request to identify which of two sample patients is most similar to the query patient. In an operation 56 the user inputted comparison values are received (e.g. the ranking of the sample patient, or the selection of the more similar sample patient of a set of two sample patients). In an operation 60, the set of features 24 and/or feature weights $w_n$ are adjusted to increase agreement of the patient comparison metric, applied to the sample patients, with the user inputted comparison values. For example, if the user ranks a sample patient as very similar to the query patient then adjusts that result in a shorter sample patient-to-query patient distance as measured by the (adjusted) patient comparison metric are accepted, while adjustments that increase this distance are rejected. In an operation 62 the clustering process 30 is repeated with the adjusted patient comparison metric. Flow then returns to the operation 54 by which the clinician is presented with similar and/or dissimilar patients in accord with the updated clustering. This loop may be repeated any number of times, until at an operation 64 the clinician reviewing the latest clustering results concludes that they are satisfactory.

In the following, some illustrative approaches are disclosed for implementing the operation 60 as automated mapping of the features from the original space to a new space where the relevant features according to the clinical expert (from operation 56) exhibit smaller distance. A first illustrative approach uses dimensionality reduction methods, while a second illustrative approach uses a feature weights adjustment method.

In the first illustrative approach employing dimensionality reduction, patient data (V) are represented that contains features $F=\{f_1, \ldots, f_n\}$ for patients $P=\{p_1, \ldots, p_m\}$. Next, distances between the patients are computed to obtain a distance matrix ($S_m$; size m×m; square, symmetric) and Classical Multidimensional Scaling (MDS) is used to obtain lower dimensional projections of this data. In an illustrative approach, MDS analysis is performed by specifying the number of dimensions from 2 through (m−1) and computing the pairwise Euclidean distances between patients $p_1, \ldots p_m$ for each lower dimensional projection to obtain distance matrices $D^{(2)}, \ldots D^{(m-1)}$. If the doctor opined in operation 56 that specific patients (groups or separate pairs) are expected to be more similar, the pairwise distances between all possible pairs in that group are minimized. We identify K in $\{2, \ldots (m-1)\}$ for which this metric is the smallest. Using matrix notation:

$$V = \begin{bmatrix} v_{p_1 f_1} & \cdots & \cdots & v_{p_1 f_n} \\ v_{p_2 f_1} & \cdots & \cdots & v_{p_2 f_n} \\ \vdots & \vdots & \vdots & \vdots \\ v_{p_m f_1} & \cdots & \cdots & v_{p_m f_n} \end{bmatrix} \text{ and}$$

$$S_m = \begin{bmatrix} d_{m(1,1)} & \cdots & \cdots & d_{m(1,m)} \\ d_{m(2,1)} & \cdots & \cdots & d_{m(2,m)} \\ \vdots & \vdots & \vdots & \vdots \\ d_{m(m,1)} & \cdots & \cdots & d_{m(m,m)} \end{bmatrix}$$

where matrix $S_m$ is symmetric ($d_{m(p,q)} = d_{m(q,p)}$; p≠q; p= $\{1, \ldots, m\}$; q=$\{1, \ldots, m\}$ and the MDS function takes distance matrix (size m×m) and number of dimensions (l; l<m). For l in the range $\{2, \ldots (m-1)\}$ compute the pairwise-distances of m points to obtain symmetric distance matrix YD. Groups of similar patients based on physician feedback are denoted as $G=\{g_1, g_2 \ldots\}$ where $g_i$ is a set of patients from P. Then:

$$D^{(l)} = \begin{bmatrix} d_{(1,1)} & \cdots & \cdots & d_{(1,l)} \\ d_{(2,1)} & \cdots & \cdots & d_{(2,l)} \\ \vdots & \vdots & \vdots & \vdots \\ d_{(l,1)} & \cdots & \cdots & d_{(l,l)} \end{bmatrix} \text{ and}$$

$$k = \min_{l \text{ in } \{2, \ldots, (m-1)\}} \sum_{\substack{g_i \text{ in } G; \\ p_a, p_b \text{ in } g_i \\ a \neq b; a < b}} D^{(l)}[a, b]$$

where k is an integer in $\{2, \ldots, (m-1)\}$ which presents the lowest dimension that places patient groups in G closest. Principal Component Analysis (PCA) or another feature reduction algorithm is used to identify the top k most important features. These k features are used to cluster new patients in the operation 62. The physician-informed group G is optionally partitioned to obtain cross-validation and prevent over-fitting issues.

The second illustrative approach for implementing the operation 60 represents the feature values in the new space by adjusting the weights of importance of these features. By way of illustration, three example patients are as follows:

Patient P1 with feature values (3, 2, 4, 7)
Patient P2 with feature values (3, 3, 3, 3)
Patient P3 with feature values (4, 3, 3, 7)

In this notation, each patient Pi has features in columns 1 through 4 with values (f1, f2, f3, f4). For illustration, the following distances are assumed:

Patient distance D(P1,P3)=3
Patient distance D(P1,P2)=6
Patient distance D(P2,P3)=5

In the initial clustering operation 52, using a Manhattan distance, the first cluster contains patients P1 and P3 and patient P2 is in a second cluster. However, the doctor in operation 56 indicates that patients P2 and P3 are viewed as being more similar, perhaps because the doctor considers features f2 and f3 to be more important, and accordingly the clustering is updated to P2 and P3 being assigned to the same cluster, and P1 belongs in a separate cluster.

The centroid of the new cluster is calculated as the average of the feature values in the cluster: Pc=(3.5, 3, 3, 5). Next, the original samples are mapped to a new space where the distance of the two samples to the centroid in the new space is minimal (could be specified upfront or could be specified by the user). To adjust the coordinates to the new space the original coordinates are multiplied with the adjusted weights for each feature (coordinate in the new space).

To solve this a set of linear equations are suitably used. However, the number of patients n and the number of features m is usually not the same. So, for the chosen number of patients p where p≤n a set of most varying features is derived that are to be mapped onto the new space. Notationally:

$$w1 * f11 + w2 * f12 + \ldots + wp * f1p = d1$$

$$w2 * f21 + w2 * f22 + \ldots + wp * f2p = d2$$

$$\ldots$$

$$wp * fp1 + wp * fp2 + \ldots + wp * f2p = d2$$

To do this, the variance for all the features is calculated and the top p varying features are chosen. The new matrix is has dimensions p×p. For this new matrix the set of linear equations is solved in order to find the appropriate weights. Once the weights are determined, the same weights are applied to the patients that were not selected by the user onto the new space.

In the foregoing example, this would translate to:

$$w1*3 + w4*3 = d1$$

$$w1*4 + w4*7 = d2$$

where it is assumed that w1 and w4 are the weights, and features in column 1 and column 4 are the ones that vary the most (for patient P1 and P2).

The foregoing are merely illustrative examples, and other approaches for performing the operation 60 are also contemplated. It is also contemplated to employ a combination of adjustments, e.g. performing a dimensionality reduction (first illustrative approach) followed by a weights adjustment (second illustrative approach); or vice versa.

Figure 3:
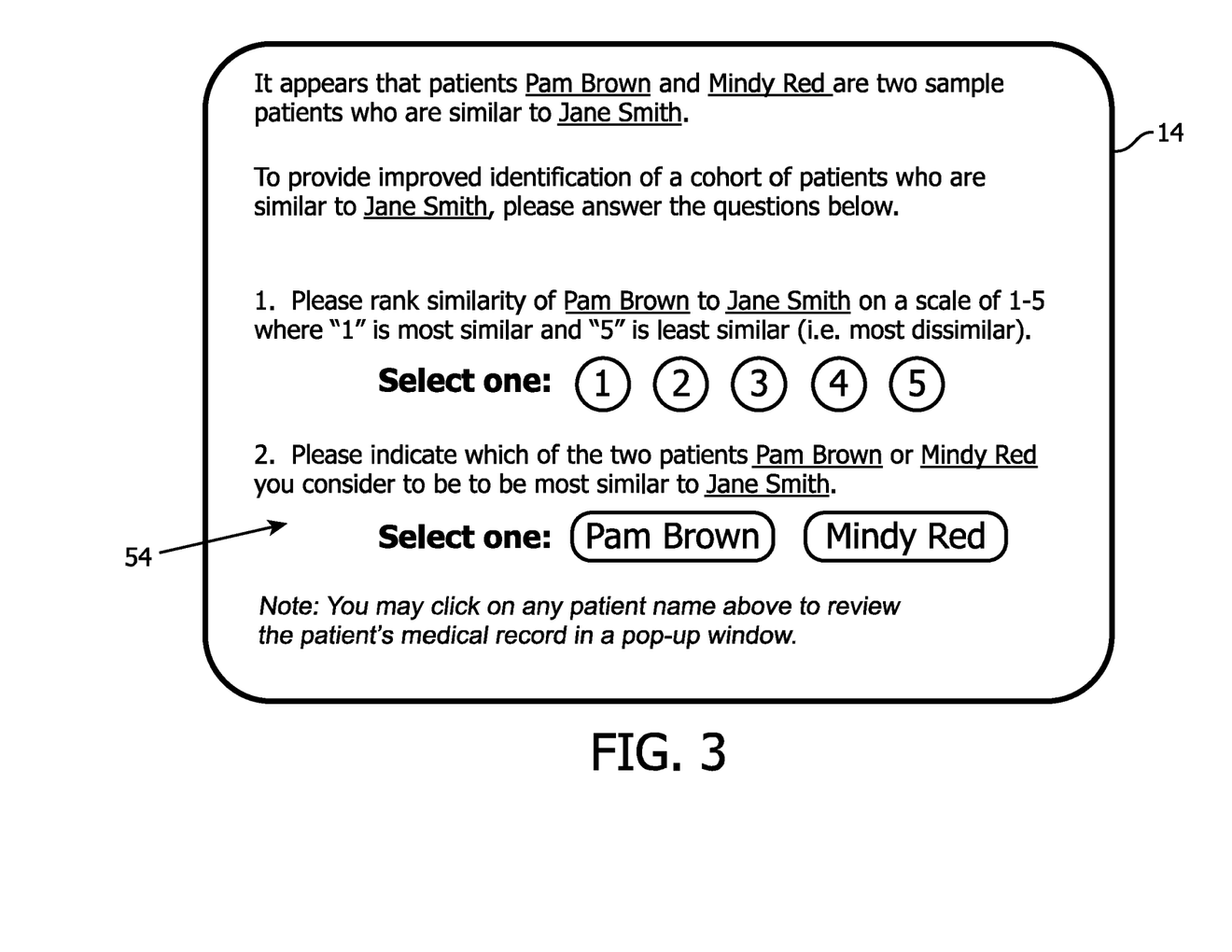
FIGS. 3 and 4 diagrammatically show two illustrative examples of suitable embodiments of the presentation operation of the method of FIG. 2.

With reference to FIG. 3, an illustrative presentation of similar sample patients on the display component 14 is shown (i.e. operation 54 of FIG. 2), for an illustrative example in which the query patient $P_Q$ is patient "John Smith" and two similar sample patients identified by the last clustering iteration are "Bob Brown" and "Mickey Red". Two relevance feedback responses are requested. The first is in the form of a request to rank similarity of "Bob Brown" to "John Smith" on a scale of 1-5 where "1" is most similar and "5" is least similar or most dissimilar. The clinician can use the mouse pointer to select one of the buttoned labeled "1" through "5" in order to answer this request. The second request is to select which of the two patients "Bob Brown" and "Mickey Red" are most similar to the query patient "John Smith". The clinician can answer this by using the mouse pointer to select either the "Bob Brown" button or the "Mickey Red" button.

To meaningfully answer these requests, it will be appreciated that the clinician will likely want to review the medical records or other patient information for the query patient "John Smith" and for each sample patient "Bob Brown" and "Mickey Red". To this end, each reference to one of these patients is shown as a hyperlink in the display of FIG. 3 (as indicated by underscoring the patient name), and the display explains: "Note: You may click on any patient name above to review the patient's medical record in a pop-up window." Thus, in response to the clinician using the mouse pointer to click on "John Smith", a pop-up window (not shown) is brought up in which patient record information on John Smith is displayed, preferably with suitable navigation tools to enable the clinician to navigate through John Smith's medical record. Analogously likewise if an occurrence of the patient name "Bob Brown" or "Mickey Red" is mouse-clicked. Such pop-up displays may include patient feature information, but the clinician is able to navigate the entire patient record and is not being asked to evaluate patient similarity on the basis of any single patient feature or small group of patient features. It will be appreciated that other navigational tool frameworks may be used, e.g. rather than a pop-up window the patient record may be displayed on a separate display component (if available; not shown in FIG. 1).

Figure 4:
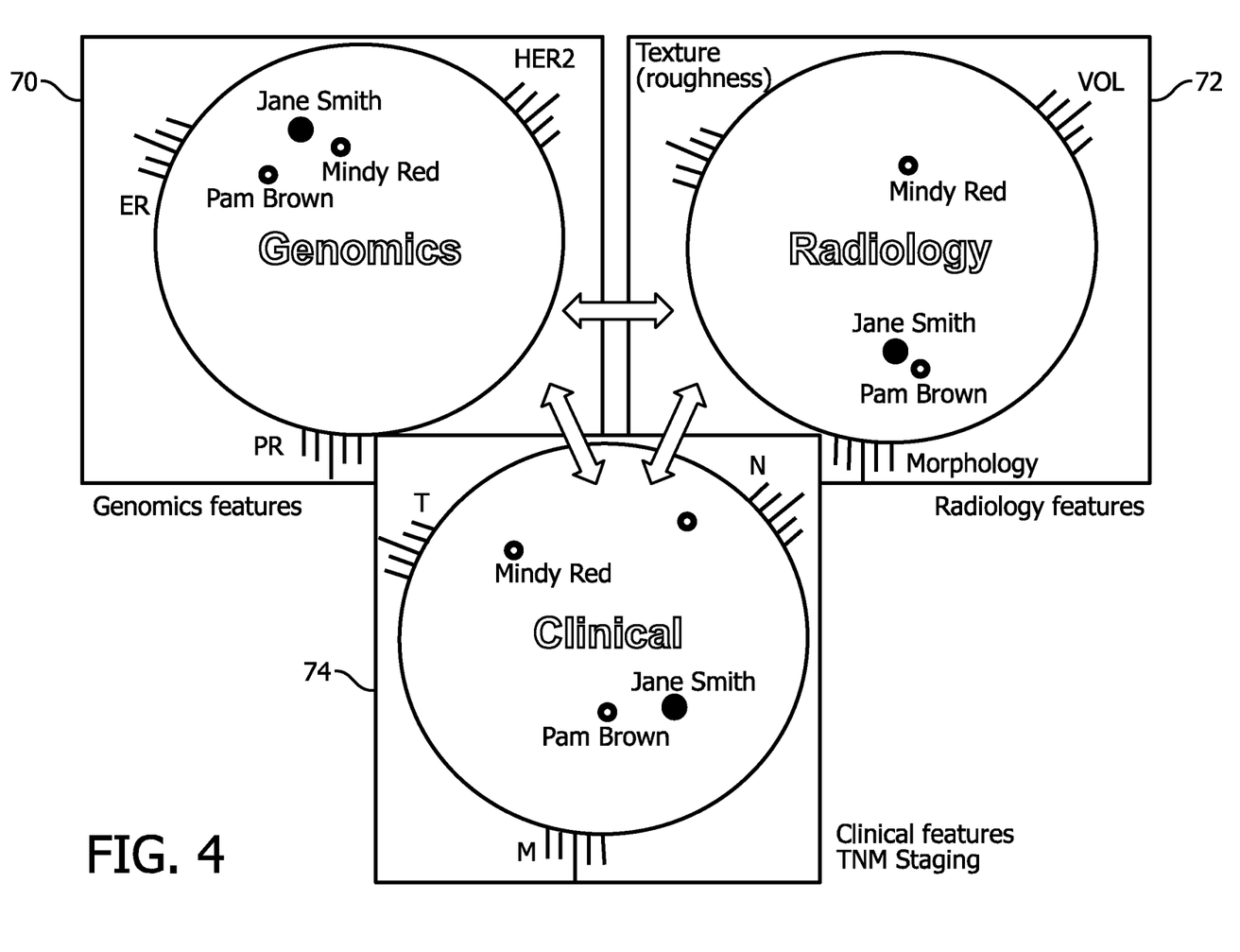

With reference to FIG. 4, in other embodiments information about the sample patients may be displayed in other ways. For example, FIG. 4 illustrates a visualization tool in which two or more graphical modality representations are simultaneously displayed on the display component 14. The illustrative example of FIG. 4 includes three simultaneously displayed graphical modality representations: one graphical modality representation 70 for the genomics modality; one graphical modality representation 72 for the radiology modality; and one graphical modality representation 74 for the clinical modality. Each graphical modality representation 70, 72, 74 plots the one or more sample patients in a waterfall plot and the query patient (in illustrative FIG. 4, the two sample patients Bob Brown and Mickey Red and the query patient John Smith) against two or more features of the modality. In illustrative FIG. 2, the genomics modality representation 70 plots the patients against the ER, HER2, and PR genomic marker features. The radiology modality representation 72 plots the patients against texture (roughness), volume, and morphology image features. The clinical modality representation 74 is for an oncology staging modality and plots the patients against the tumor size (T), nodal status (N), and metastasis value (M) tumor features. From FIG. 4, the clinician can readily observe that, for the represented features, sample patient Bob Brown appears to be more similar to query patient John Smith as compared with sample patient Mickey Red.

Figure 5:
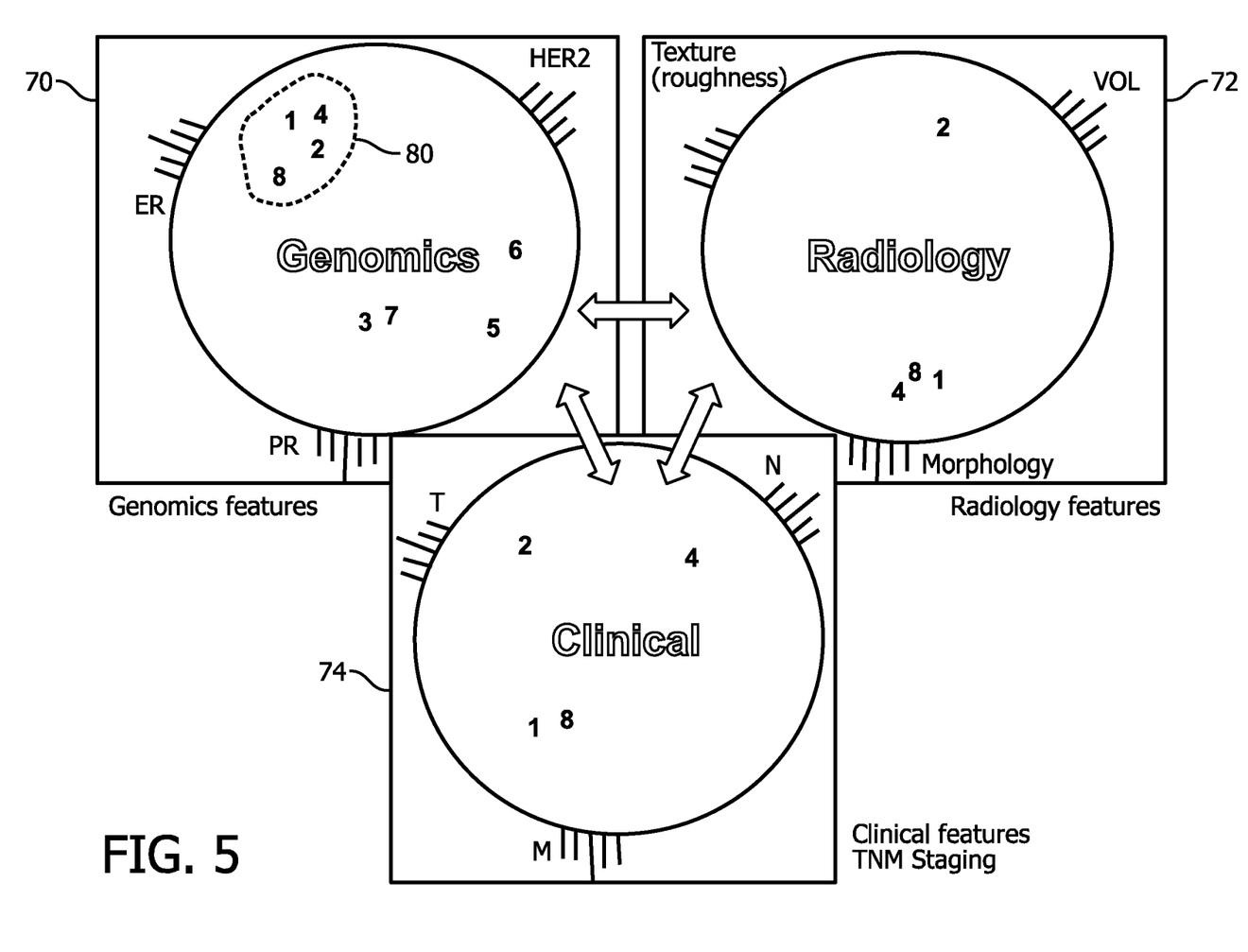
FIG. 5 diagrammatically shows a patient cohort visual representation and navigation tool as described herein.

With reference to FIG. 5, it is noted that the visual representation of FIG. 4 is more generally applicable, and can be used to navigate the patient database 20 to identify patient cohorts by interactive graphical visualization. In the illustrative example of FIG. 5, the same genomics, radiology, and clinical modality representations 70, 72, 74 of FIG. 4 are again displayed. In the genomics modality representation 70, the GUI process 40 (see FIG. 1) has received a selection of a cluster of patients (designated arbitrarily as patients {1, 2, 4, 8} by a suitable selection method such as individually clicking on each patient of the cluster or, in the illustrative example, by receiving an encirclement 80 of the cluster of patients {1, 2, 4, 8} via at least one user input device (e.g. the mouse 18, or a trackball, trackpad, touchscreen, or other pointing device). In each of the other simultaneously displayed modality graphical representations 72, 74, in response to the selection 80 the patients of the selected cluster of patients {1, 2, 4, 8} are also highlighted. In illustrative FIG. 5 this highlighting is done in the other-modality graphical representations 72, 74 by removing display of all other patients so that only the patients 1, 2, 4, and 8 are displayed. The highlighting can use other approaches, such as displaying the patients of the selected cluster in red and continuing to display all other patients in black.

As seen in FIG. 5, the patients 1, 4, and 8 also cluster well in the radiology graphical representation 72, whereas the patient 2 is an outlier in this modality view. In the clinical modality graphical representation 74 only the patients 1 and 8 cluster together while patients 2 and 4 are outliers. Based on these results, the clinician may be able to draw various conclusions. For example, if the query patient is patient 1, then patient 8 may be determined to be the closest patient to query patient 1 (since patient 8 is close to patient 1 in all three views), while patient 2 is seen to be most dissimilar. In another view, the clinician may decide to try changing one or more of the representations 72, 74 by updating the two or more coordinate features in response, the GUI process 40 re-draws the graphical modality representation updated to plot patients against the updated two or more coordinate features of the modality.

While FIGS. 4 and 5 illustrate a visualization example for genomics, radiology, and clinical modalities, the various graphical modality representations may more generally include modalities such as clinical, radiology, genomics, demographic, and/or physiological modalities. In general, the user may choose which modalities to display from a palette or list of available modalities, and can further select which features of each modality to plot against.

In the following, a more detailed illustrative visual representation and navigation process suitably performed by the GUI process 40 of FIG. 1 using two or more graphical modality representations such as the representations 70, 72, 74 of FIGS. 4 and 5 is described. The approach begins by selecting a query patient, e.g. via a search for name or electronic medical record (EMR) number. Basic information for this patient may be displayed, such as name, age, primary physician, disease, et cetera. A user workspace is displayed containing the graphical modality representations 70, 72, 74. In the illustrative example of FIGS. 4 and 5, each modality representation is presented as a circle, with the modality features against which patients are plotted placed at equal intervals around the circle (such as the presence of biomarkers associated with a particular disease in the case of a genomics modality). Other patients are automatically integrated into this visualization, pulled from any available cohorts (e.g., generated using the patient cohort identification device of FIG. 1) to populate the circle. This places the patient of interest in the context of a greater population of patients. By default, all modalities are displayed simultaneously, but each can be zoomed in to inspect individually. The features placed along the periphery of the circle (i.e., features plotted against) can be selected. Any values tied to the patient that value is assigned to are subsequently highlighted across all available modalities. Subsequent analyses can be performed on these select patients.

Optionally, as the user selects the patients, a statistical summary is displayed on the screen that highlights salient properties of the selected patients. This summary is updated dynamically as the selection of patients is updated. The content of the summary can be described based on the nature of the variable; discrete or continuous.

Given the large number of available demographic, pathologic, clinical and genomic features (e.g., 200 or more in some patient databases) a navigation tool is provided that supports selection of features, such as biomarkers, signatures, prognostic scores, etc. and cohort samples, for the effective summarization and visualization of data relevant to specific contexts of interests. Optionally, the GUI tool also allows the clinician to define and save customized selections, and easily switch from one context to another.

In the illustrative example of FIG. 5, the clinician views the ER, HER2, and PR receptor statuses in the genomics graphical view 70 of a selected patient in the context of other patients in the database or a chosen cohort, and has the flexibility to view the same patients in other-modality graphical views 72, 74. The clinician can select/highlight a subset of the patients that is interesting from the genomic view, e.g. using the encirclement 80, and these patients are highlighted in the other views 72, 74. Thus, for example, the T,N,M staging of the selected patients {1, 2, 4, 8} is viewed in the clinical (cancer staging) graphical view 74, so as to assess the distribution of T (tumor size), N (nodal status), and M (Metastasis status) distributions of the selected patients. (It will be appreciated that a more well-defined distribution will likely be obtained if the number of selected patients is greater than the illustrative example of four selected patients). Similarly, in the imaging graphical view 72, MRI features e.g. volume, wash-in, wash-out characteristics, texture, and morphology features are shown. Other modality views can be selected by the clinician (not shown). In this way, the clinician can interactively test for association of a feature or group of features in one modality for a selected group of patients between different modalities.

As a further example, the genomics graphical view 70 is described in further detail. The genomics layer is displayed on a circle, as seen in FIG. 5, where an example suitable for the task of assessing breast cancer is specifically shown. For this task, features of interest include the ER, PR, and HER2 activity levels which have demonstrated clinical utility for breast tumor diagnosis and prognosis. (Naturally, other salient genomic features will be selected to plot against for other tasks). When the clinician opens the application it will display the patient of interest (query patient) along with other patients in the selected cohort (e.g., generated using the cohort identification device of FIG. 1). In illustrative FIG. 5, three waterfall plots (bars plotted in descending order) are shown, each representing one of ER/PR/HER2 activity, placed evenly across the genomics circle 70. In one navigation approach, the query patient is automatically selected to highlight the query patient's activity levels for each biomarker on the circle relative to the rest of the cohort. Lines (not shown) are optionally drawn from these three bars representing the patient to a region in the center of the circle, where a machine learning algorithm (such as Principle Component Analysis), calculated from the ER/PR/HER2 data of the cohort, has been appropriately visualized. The lines are drawn precisely to where the patient of interest lies relative to the cohort. From this overall visualization, additional patients having similar ER/PR/HER2 expression levels are selected, e.g. using the encirclement 80. Any additional patients selected in the machine learning space would have lines drawn to their respective ER/PR/HER2 activity levels surrounding the circle.

Statistical summaries may also be provided for the selected group (e.g. group {1, 2, 4, 8} in FIG. 5). For continuous variables such as age and expression values of genes, the average of the selected group may be calculated. For discrete variables such as gender and ER status, an enrichment analysis using tests such as Hyper-geometric test may be performed and the properties sorted in a descending order of the p-values. A typical summary of selected patients for a Breast Cancer dataset is shown in Table 1.

TABLE 1

| Summary of selected patients for a Breast Cancer dataset | |
|---|---|
| Mean age | 46 |
| Mean expression value of P53 | 2.3 FPKM |
| Dominant gender | Female (p-value 0.001) |
| Dominant ER status | Positive (p-value 0.003) |
| Dominant PR status | Negative (p-value 0.005) |
| Dominant HER2 status | Positive (p-value 0.007) |
| Dominant breast cancer subtype | Basal (p-value 0.009) |

In this table, the FPKM (fragments per kilobase of exon per million reads mapped) signifies the expression value of the p53 gene based on RNA sequencing data. A significant number of these variables are specific to the illustrative task of breast cancer diagnosis, and the statistical summary elements are suitably pre-described in the summary format for each disease or clinical task.

The graphical visualization and navigation tool of FIGS. 4 and 5 is an illustrative example. Other geometries besides the illustrative circular geometry can be employed. An advantage of the circular geometry is that it is readily updated to a reasonable number of modality features to be plotted against (i.e., any number of features that can be comfortably fitted around the circle); whereas, for example, a square geometry is only well-suited for plotting against two modality features.

It is also contemplated that the operation of selecting a cluster of patients in one graphical modality representation may be performed by an entity/mechanism other than the clinician operating the user input device(s) 16, 18 (e.g., to make the encirclement selection 80 as in FIG. 5). For example, in the illustrative example of FIG. 4, another program executing on the computer 10, 12, e.g. the clustering process 30, selects the cluster of patients as the query patient and the set of one or more sample patients (sample patients Bob Brown and Mickey Red and query patient John Smith in illustrative FIG. 4).

With returning reference to FIGS. 1 and 2, another illustrative implementation of the patient cohort identification using patient-level relevance feedback is described textually below, and includes the following steps:

Step 1. Perform unsupervised learning using hierarchical clustering on all the patients and selected patient features on a large data set (greater than one million samples in some embodiments).

Step 2. Determine the number of clusters and calculate cluster centroids.

Step 3. Choose the cluster containing the query patient $P_Q$ based on all the features, and select additional seeds from the same cluster.

Step 4. For each seed find the most similar patients based on the distance of this patient to all the different cluster centroids as measured using the patient comparison metric.

Step 5. Select the sample and the similar samples to the current sample based on the prioritized list of similar patients (e.g. of the ones that belong to a single cluster).

Step 6. Determine which features are making this similarity of the patients important by removing one feature at a time.

Step 7. Find the distance between the current patient and all the selected patients using the patient comparison metric.

Step 8. Find columns whole median is close to 0. Discard columns with high numbers.

Step 9. Based on the selected features perform unsupervised clustering on the entire dataset just using the selected clustering.

Step 10 Present at the end the patients that are in the cluster of the original query patient $P_Q$, or where the majority of the selected patients appear.

Finally, repeat the above Steps 1-10 iteratively until the set of samples is all relevant to the clinician.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A patient cohort identification device comprising:
a computer having a display component and at least one user input device, the computer being in communication with a patient database storing patient data comprising values of features for patients in the patient database, the computer programmed to perform a patient cohort identification method including:
performing an automatic feature selection process on the patient data to select a set of features and automated clustering of patients of the patient database using a patient comparison metric dependent on the set of features, wherein the automatic feature selection process is an unsupervised feature selection process, and wherein the automated clustering comprises generating a plurality of clusters including at least a first cluster of patients of the patient database similar to a query patient and at least a second cluster of patients of the patient database dissimilar to a query patient;
performing at least one iteration of:
displaying, on the display component, information on a plurality of sample patients, the plurality of sample patients including (i) one or more patients from the first cluster who are similar to the query patient according to the automated clustering, and (ii) one or more patients from the second cluster who are dissimilar to the query patient according to the automated clustering;
receiving, via the at least one user input device, user-inputted comparison values comparing one or more of the plurality of sample patients with the query patient, wherein the user-inputted comparison values comprise a comparison of the query patient and the plurality of sample patients at a patient level rather than a feature level using the set of features, and comprise either: (i) a ranking of similarity of the plurality of sample patients relative to the query patient or (ii) a selection of one or more of plurality of patients most similar to the query patient;
adjusting the patient comparison metric to increase agreement between the user-inputted comparison values and comparison values computed by the patient comparison metric comparing the one or more sample patients with the query patient, wherein the adjusting including adjusting at least one of the set of features and feature weights of the patient comparison metric; and
repeating the automated clustering using the adjusted patient comparison metric; and
identifying a patient cohort for the query patient using the adjusted patient comparison metric produced by a last iteration of the last least one iteration.

2. The patient cohort identification device of claim 1 wherein the identifying includes:
identifying the patient cohort as at least part of a cluster containing the query patient that was generated by the last repetition of the automated clustering.

3. The patient cohort identification device of claim 1 wherein the displaying and receiving comprises at least one of:
(I) displaying, on the display component, information on one or more similar sample patients belonging to a cluster also containing the query patient that was generated by the most recently-performed automated clustering; or
(II) displaying, on the display component, information on or more dissimilar sample patients not belonging to a cluster also containing the query patient that was generated by the most recently-performed automated clustering.

4. The patient cohort identification device of claim 1 wherein the displaying and receiving comprises, for at least one sample patient:
(I) displaying a request to rank similarity of at least one sample patient to the query patient on a quantitative ranking scale; and
receiving the user inputted comparison value for the sample patient as a received similarity ranking of the sample patient on the quantitative ranking scale; and
(II) displaying a request to select which of the two sample patients is most similar to the query patient; and
receiving a user inputted comparison value as a received selection of which of the two samples patients is most similar to the query patient.

5. The patient cohort identification device of claim 1 wherein the displaying comprises:
simultaneously displaying two or more graphical modality representations in which each graphical modality representation plots the one or more sample patients and the query patient against two or more features of the modality, preferably the two or more graphical modality representations include graphical modality representations for modalities selected from a group consisting of: clinical, radiology, genomics, demographic, and physiological modalities.

6. The patient cohort identification device of claim 1 wherein the adjusting comprises:
(I) performing a plurality of feature set adjustment iterations each including:
(1) adjusting the set of features by adding or removing a feature to produce a candidate adjusted set of features;

(2) computing comparison values using the patient comparison metric with the candidate adjusted set of features that compare the one or more sample patients with the query patient;

(3) accepting or rejecting the candidate adjusted set of features based on whether the comparison values computed in operation are in increased or decreased agreement, respectively, with the user-inputted comparison values; or (II) performing dimensionality reduction to reduce the number of features in the feature set.

7. The patient cohort identification device of claim 1 wherein the adjusting comprises adjusting feature weights of the patient comparison metric, preferably the adjusting comprises performing a plurality of feature weight adjustment iterations each including:

(1) adjusting the patient comparison metric by increasing or decreasing the value of at least one feature weight of the patient comparison metric to produce a candidate adjusted patient comparison metric;

(2) computing comparison values using the candidate adjusted patient comparison metric that compare the one or more sample patients with the query patient; and (3) accepting or rejecting the candidate adjusted patient comparison metric based on whether the comparison values computed in operation are in increased or decreased agreement, respectively, with the user-inputted comparison values.

8. The patient cohort identification device of claim 1 wherein the automatic feature selection process is one of Principal Component Analysis (PCA), information gain (IG), and pairwise feature correlation.

9. The patient cohort identification device of claim 1, wherein the one or more patients from the second cluster who are dissimilar to the query patient are selected for inclusion in the plurality of sample patients from a second cluster where a centroid of the second cluster is furthest from the query patient as measured by the patient comparison metric.

10. A patient cohort identification method performed in conjunction with a computer having a display component and at least one user input device and in communication with a patient database storing patient data comprising values of features for patients in the patient database, the patient cohort identification method including:

performing automated clustering of patients of the patient database using a patient comparison metric dependent on a set of features, wherein the automated clustering comprises an unsupervised feature selection process, and wherein the automated clustering comprises generating a plurality of clusters including at least a first cluster of patients of the patient database similar to a query patient and at least a second cluster of patients of the patient database dissimilar to a query patient;

performing at least one iteration of:

displaying, on the display component, information on a plurality of sample patients, the plurality of sample patients including (i) one or more patients from the first cluster who are similar to the query patient according to the automated clustering, and (ii) one or more patients from the second cluster who are dissimilar to the query patient according to the automated clustering;

receiving, via the at least one user input device, user-inputted comparison values comparing one or more of the plurality of sample patients with the query patient, wherein the user-inputted comparison values comprise a comparison of the query patient and the plurality of sample patients at a patient level rather than a feature level using the set of features, and comprise either: (i) a ranking of similarity of the plurality of sample patients relative to the query patient or (ii) a selection of one or more of plurality of patients most similar to the query patient;

adjusting at least one of the set of features and feature weights of the patient comparison metric to generate an adjusted patient comparison metric having improved agreement with the user-inputted comparison values as compared with the patient comparison metric without the adjusting; and repeating the automated clustering using the adjusted patient comparison metric; and identifying a patient cohort for the query patient as at least part of a cluster containing the query patient produced by the automated clustering repetition of a last iteration of the last least one iteration.

11. The patient cohort identification method of claim 10 wherein the displaying and receiving comprises at least one of:

(I) displaying a request to rank similarity of a sample patient to the query patient on a quantitative ranking scale and receiving a similarity ranking of the sample patient on the quantitative ranking scale; and (II) displaying a request to select which of two sample patients is most similar to the query patient and receiving a selection of which of the two sample patients is most similar to the query patient.

12. The patient cohort identification method of claim 10 wherein the displaying comprises:

simultaneously displaying two or more graphical modality representations in which each graphical modality representation plots the one or more sample patients and the query patient against two or more features of the modality.

13. The patient cohort identification method of claim 10, wherein the one or more patients from the second cluster who are dissimilar to the query patient are selected for inclusion in the plurality of sample patients from a second cluster where a centroid of the second cluster is furthest from the query patient as measured by the patient comparison metric.

* * * * *